United States Patent [19]

Kwon

[11] Patent Number: 5,474,758
[45] Date of Patent: Dec. 12, 1995

[54] SEALS FOR USE IN AN AEROSOL DELIVERY DEVICE

[75] Inventor: Oh-Seung Kwon, Woodbury, Minn.

[73] Assignee: Minnesota Mining and Manufacturing Company, St. Paul, Minn.

[21] Appl. No.: 98,605

[22] Filed: Jul. 28, 1993

[51] Int. Cl.$^6$ .............................. A61K 9/12; B65D 83/54
[52] U.S. Cl. .................... 424/45; 222/394; 222/402.1; 424/46; 239/337
[58] Field of Search .................... 424/43, 45, 46; 222/373, 402.1, 394, 398; 239/338, 337; 252/305

[56] References Cited

U.S. PATENT DOCUMENTS

| | | | |
|---|---|---|---|
| 2,721,010 | 10/1955 | Meshberg | 222/394 |
| 2,886,217 | 5/1959 | Thiel | 222/394 |
| 2,892,576 | 6/1959 | Ward | 222/394 |
| 2,968,427 | 1/1961 | Meshberg | 222/394 |
| 2,980,301 | 4/1961 | de Gorter | 222/394 |
| 3,049,269 | 8/1962 | Gawthrop | 222/307 |
| 3,052,382 | 9/1962 | Gawthrop | 222/335 |
| 3,702,310 | 11/1972 | Simons et al. | 252/430 |
| 3,727,806 | 4/1973 | Wilmont | 222/402.2 |
| 4,243,235 | 1/1981 | Repella | 277/152 |
| 4,343,918 | 8/1982 | Bohm et al. | 525/194 |
| 4,386,179 | 5/1983 | Sterling | 524/269 |
| 4,407,481 | 10/1983 | Bolton et al. | 251/353 |
| 4,481,323 | 11/1984 | Sterling | 524/269 |
| 4,511,354 | 4/1985 | Sterling | 604/98 |

(List continued on next page.)

FOREIGN PATENT DOCUMENTS

| | | |
|---|---|---|
| 0393993 | 10/1990 | European Pat. Off. . |
| 0534308 | 3/1993 | European Pat. Off. . |
| 2532714 | 3/1984 | France . |
| 6320309 | 7/1986 | Japan . |
| 3-269081 | 11/1991 | Japan . |
| 4110381 | 4/1992 | Japan . |
| 2033910 | 5/1980 | United Kingdom . |
| 2077229 | 12/1981 | United Kingdom . |
| 2246605 | 2/1992 | United Kingdom . |
| 91/11495 | 8/1991 | WIPO . |
| 91/09726 | 7/1992 | WIPO . |
| 93/04328 | 11/1993 | WIPO . |

OTHER PUBLICATIONS

World Patents Index Latest, Derwent Publications Ltd., London, GB, AN 85–259656 & JP,A,60173047 (Dainippon) 1985.
"Minimal–Diblock–Content SBCs Provide Formulating Flexibility", *Adhesives Age*, 1990 (Jagisch et al.).
"Biomedical TPEs are High in Clarity and Resilience", *Modern Plastics*, 1986 (Perrin et al.).
"New Silicone Modified TPE's Replace Latex, Polyurethanes and Silicone", *The Torch*, vol. 10, No. 4 (Carew et al.), 1985.
"Custom Molding & Extruding", Concept Polymer Technologies, Inc., 1987.
"New Silicone Modified TPE's for Medical Applications", Concept Polymer Technologies, Inc. (Deisler et al.), 1986.
Concept Polymer Technologies, Inc. Product Literature, 1987.
KRATON® Rubber Product Literature, 1988.
Union Carbide FLEXOMER™ Polyolefin Product Literature, 1990.

*Primary Examiner*—Raj Bawa
*Attorney, Agent, or Firm*—Gary L. Griswold; Walter N. Kirn; Robert H. Brink

[57] ABSTRACT

A device for delivering an aerosol, comprising: a casing member, a valve stem, and a diaphragm. The diaphragm contains a blend of (a) 100 parts by weight of a polyolefin random copolymer of about 80 to about 95 mole percent ethylene and a total of about 5 to about 20 mole percent of 1-butene, and (b) at least 10 parts by weight of a rubber comprising a styrene-ethylene/butylene-styrene block copolymer based on 100 parts by weight of polyolefin. The styrene-ethylene/butylene-styrene block copolymer is substantially uniformly dispersed within the polyolefin. The blend preferably has a Shore A hardness of 65 to 85.

15 Claims, 1 Drawing Sheet

U.S. PATENT DOCUMENTS

| | | | |
|---|---|---|---|
| 4,526,385 | 7/1985 | Wheeler | 277/153 |
| 4,613,640 | 9/1986 | Deisler et al. | 524/264 |
| 4,668,752 | 5/1987 | Tominari et al. | 526/348.2 |
| 4,744,495 | 5/1988 | Warby | 222/402.16 |
| 4,819,834 | 4/1989 | Thiel | 222/355 |
| 4,822,855 | 4/1989 | Kobayashi et al. | 525/194 |
| 4,863,073 | 9/1989 | Burt et al. | 222/402.2 |
| 4,867,352 | 9/1989 | Meshberg | 222/402.16 |
| 4,894,266 | 1/1990 | Bauer et al. | 428/35.4 |
| 4,944,433 | 7/1990 | Knecht et al. | 222/402.2 |
| 5,061,247 | 10/1991 | Akaike et al. | 604/187 |
| 5,118,494 | 6/1992 | Schultz et al. | 424/45 |
| 5,126,123 | 6/1992 | Johnson | 424/45 |
| 5,157,082 | 10/1992 | Johnson | 525/237 |
| 5,182,097 | 1/1993 | Byron et al. | 424/45 |
| 5,190,029 | 3/1993 | Byron et al. | 128/200.14 |

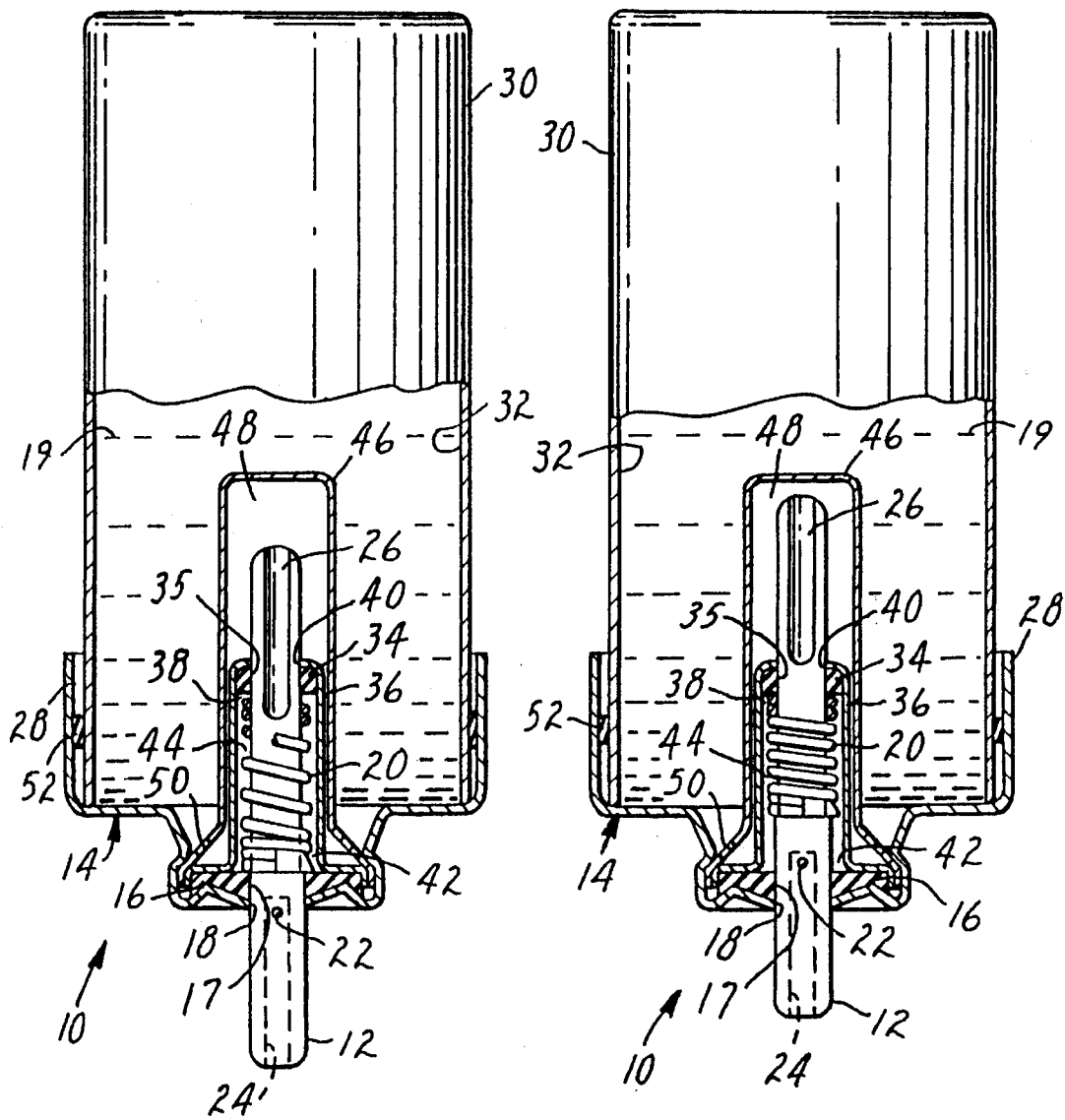

5,474,758

SEALS FOR USE IN AN AEROSOL DELIVERY DEVICE

TECHNICAL FIELD

This invention relates to devices for delivering aerosols. In another aspect this invention relates to sealing members. In yet another aspect this invention relates to sealing members for use in devices for delivering aerosols.

DESCRIPTION OF THE RELATED ART

The continuing use of aerosol formulations comprising conventional chlorofluorocarbon propellants is being debated due to the suspected role of such propellants in atmospheric depletion of ozone. Accordingly, formulations based on alternative propellants such as HFC-134a (1,1,1,2-tetrafluoroethane) and HFC-227(1,1,1,2,3,3,3-heptafluoropropane) are being developed to replace those conventional propellants thought to contribute to atmospheric ozone depletion.

Containers for aerosol formulations commonly comprise a vial body coupled to a valve ferrule. The valve ferrule comprises a valve stem through which the formulation is dispensed. Generally the valve ferrule includes a rubber valve seal (a diaphragm) intended to allow reciprocal movement of the valve stem while preventing leakage of propellant from the container. These rubber valve seals are commonly made of thermoset rubbers such as butyl rubber, butadiene-acrylonitrile ("Buna") rubbers, and neoprene (polychloroisoprene), which are compounded with vulcanizing agents prior to being fashioned into valve seals.

It has been found that some conventional devices for delivering aerosols suffer impaired performance when used in connection with HFC-134a or HFC-227. Selection of suitable materials for use as diaphragms to contain aerosol formulations based on these alternative propellants is complicated by interactions between the seal material and the formulation components, including the propellant. Conventional devices involving diaphragms of neoprene (polychloroprene), butyl rubber, or butadiene-acrylonitrile "buna" rubbers allow substantial leakage of HFC-134a or HFC-227 from some formulations over time. Particularly in low volume formulations such as pharmaceutical formulations for use in inhalation therapy, this leakage can cause a substantial increase in concentration of the active ingredient in the formulation, resulting in delivery of an improper dose. Furthermore, with some formulations the valve stem tends to stick, pause, or drag during the actuation cycle.

Certain thermoplastic elastomers have found use as improved seal materials in aerosol canisters. For example, valve seals comprising certain styrene-ethylene/butylene-styrene block copolymers are disclosed in commonly assigned copending application 07/878,041. Also, valve seals comprising certain copolymers of ethylene and either butene, hexene, or octene are disclosed in PCT US91/09726 (Marecki).

SUMMARY OF THE INVENTION

This invention provides a device for delivering an aerosol, comprising: a valve stem, a diaphragm having walls defining a diaphragm aperture, and a casing member having walls defining a casing aperture, wherein the valve stem passes through the diaphragm aperture and the casing aperture and is in slidable sealing engagement with the diaphragm aperture, and wherein the diaphragm is in sealing engagement with the casing member and comprises a blend comprising (a) 100 parts by weight of a polyolefin random copolymer comprising about 80 to about 95 mole percent ethylene and a total of about 5 to about 20 mole percent of 1-butene, and (b) at least 10 parts by weight of a rubber comprising a styrene-ethylene/butylene-styrene block copolymer based on 100 parts by weight of polyolefin, and wherein the styrene-ethylene/butylene-styrene block copolymer is uniformly dispersed within the polyolefin. The blend preferably has a Shore A hardness of 65 to 85.

This invention also provides a metered-dose device for delivering an aerosol that comprises, in addition to the above-discussed valve stem, diaphragm, and casing member, a tank seal having walls defining a tank seal aperture, and a metering tank of a predetermined volume and having an inlet end, an inlet aperture, and an outlet end, wherein the outlet end is in sealing engagement with the diaphragm, the valve stem passes through the inlet aperture and the tank seal aperture and is in slidable engagement with the tank seal aperture, and the tank seal is in sealing engagement with the inlet end of the metering tank, and wherein the valve stem is movable between an extended closed position, in which the inlet end of the metering tank is open and the outlet end is closed, and a compressed open position in which the inlet end of the metering tank is substantially sealed and the outlet end is open.

In a preferred embodiment the casing member defines a formulation chamber, and in a further preferred embodiment the formulation chamber contains an aerosol formulation comprising a propellant, said propellant comprising 1,1,1,2-tetrafluoroethane or 1,1,1,2,3,3,3-heptafluoropropane.

This invention also provides a device for delivering an aerosol, comprising: a valve stem, a diaphragm as defined above and having walls defining a diaphragm aperture, and a casing member having walls defining a formulation chamber and a casing aperture, wherein the valve stem passes through the diaphragm aperture and the casing aperture and is in slidable sealing engagement with the diaphragm aperture, and wherein the diaphragm is in sealing engagement with the casing member, the device having contained in the formulation chamber thereof a medicinal aerosol formulation, and wherein the diaphragm is stable to dimensional change when exposed to the medicinal aerosol formulation.

Devices of this invention find particular use in connection with aerosol formulations involving HFC-134a or HFC-227 as a propellant. In particular, the devices of the invention avoid or minimize the occurrence of "sidestreaming" wherein the propellant leaks through the interface between the diaphragm and the valve stem upon firing. Also, leakage and smoothness of operation are improved with some formulations in devices of the invention compared to devices involving conventional thermoset rubber diaphragms.

BRIEF DESCRIPTION OF THE DRAWINGS

The drawing is represented by FIGS. 1 and 2.

FIG. 1 is a partial cross-sectional view of one embodiment of a device of the invention, wherein the valve stem is in the extended closed position.

FIG. 2 is a partial cross-sectional view of the embodiment illustrated in FIG. 1, wherein the valve stem is in the compressed open position.

DETAILED DESCRIPTION OF THE INVENTION

As used herein the term "stable to dimensional change when exposed to 1,1,1,2-tetrafluoroethane" means that a diaphragm having a thickness of about 1.0 mm (0.040 inch), an inside diameter of about 2.5 mm (0.10 inch), and an outside diameter of about 8.6 mm (0.34 inch) will maintain its original inside and outside diameter within eight percent (or less if a lesser percentage is stated) when soaked (i.e., submerged) in 1,1,1,2-tetrafluoroethane for 21 days at 20° C. and analyzed according to the Swelling Test Method set forth below. Likewise a material stable to dimensional change when exposed to any other substance (e.g., HFC-227 or an aerosol formulation) is defined in the same manner but using the particular substance as the soaking liquid.

In order to minimize and/or prevent leakage of propellants or other formulation components, especially propellants such as 1,1,1,2-tetrafluoroethane and 1,1,1,2,3,3,3,-heptafluoropropane, from a sealed chamber, this invention provides a device comprising a sealing member. The sealing member is in the form of a diaphragm for use in connection with an aerosol formulation, preferably a pharmaceutical aerosol formulation, and preferably exhibits a leak rate of less than about 500 mg/year, more preferably less than about 300 mg/year when tested according to the Leak Rate Test Method set forth below.

A sealing member for use in a device of the invention comprises a blend comprising a polyolefin component. This component comprises a copolymer of about 80 to about 95 mole percent ethylene and a total of about 5 to about 20 mole percent of 1-butene. These random copolymers preferably have a density between about 0.87 g/cm$^3$ and about 0.92 g/cm$^3$. Shore A hardness is preferably between about 40 and about 95, more preferably between about 50 and about 75. The preferred melt index range is about 0.8g/10 min to about 2.0 g/10 min (ASTM D 1238).

A preferred material is FLEXOMER™ DFDB 1085 polyolefin (Union Carbide), comprising a copolymer of about 80 mole percent ethylene and about 20 mole percent 1-butene, having a density of 0.884 g/cm$^3$ (ASTM D-1505) and a melt index of about 0.8g/10 min (ASTM D 1238).

Other materials suitable for inclusion in the polyolefin include: FLEXOMER™ DFDA 1138 NT polyolefin (commercially available from Union Carbide), a polyolefin comprising a copolymer of about 91 mole percent ethylene and about 9 mole percent 1-butene and having a density of 0.900 g/cm$^3$ (ASTM D-1505) and a melt index of 0.4 g/10 min (ASTM D-1238);

FLEXOMER™ DFDA 1137 NT7 polyolefin (commercially available from Union Carbide), a thermoplastic elastomer comprising a copolymer of about 91 mole percent ethylene and about 9 mole percent 1-butene. This copolymer is said to have a density of 0.905 g/cm$^3$ (ASTM D-1505) and a melt index of 1.0 g/10 min (ASTM D-1238);

FLEXOMER™ 1491 NT7 polyolefin (Union Carbide), comprising a copolymer of about 90 mole percent ethylene and about 10 mole percent 1-butene, having a density of 0.900 g/cm$^3$ (ASTM D 1505) and a melt index of about 1.0 g/10 min (ASTM D 1238);

FLEXOMER™ 9020 NT7 polyolefin (Union Carbide), comprising a copolymer of about 92 mole percent ethylene and about 8 mole percent 1-butene, having a density of 0.905 g/cm$^3$ (ASTM D 1505) and a melt index of about 0.85 g/10 min (ASTM D 1238); and FLEXOMER™ 9042 NT polyolefin (Union Carbide), comprising a copolymer of about 80 mole percent ethylene and about 20 mole percent 1-butene, having a density of 0.900 g/cm$^3$ (ASTM D 1505) and a melt index of about 5.0 g/10 min (ASTM D 1238).

Blends of two or more of the above-described polyolefins can also be used.

Suitable polyolefins of this type can be prepared using methods known to those skilled in the art.

A sealing member for use in a device of the invention also comprises at least 10 parts by weight (based on 100 parts by weight of the polyolefin component) of a rubber comprising a styrene-ethylene/butylene-styrene block copolymer (a SEBS copolymer). The rubber optionally further comprises a polyolefin, e.g., polypropylene, and further optionally comprises a siloxane such as polydimethylsiloxane or polymethyloctylsiloxane. These block copolymers preferably have a density between about 0.87 g/cm$^3$ and about 0.97 g/cm$^3$, more preferably between about 0.89 g/cm$^3$ and 0.91 g/cm$^3$. Shore A hardness is preferably between about 40 and about 95, more preferably between about 50 and about 75.

Certain suitable rubbers of this type are commercially available. Others can be prepared using methods known to those skilled in the art and disclosed, e.g., in U.S. Pat. Nos. 4,386,179, 4,481,323, and 4,511,354, all incorporated herein by reference, and in "Thermoplastic Elastomers, A Comprehensive Review", N. R. Legge et al., Ed., Hanser Publishers, New York, 1987, pp. 47–66. Preferred rubbers include:

KRATON™ G rubbers (Shell Chemical Co., Houston, TX) such as:

KRATON G 1657 rubber, a material comprising a SEBS copolymer having a styrene to ethylene/butylene ratio of 13/87 and containing about 35% styrene-ethylene/butylene diblock copolymer, having a Shore A hardness of 65;

KRATON G-1651 rubber, a material comprising a SEBS copolymer having a styrene to ethylene/butylene ratio of 32/68;

KRATON G-1650 rubber, a SEBS copolymer having a styrene-ethylene/butylene ratio of 29/71, having a Shore A hardness of 75 and a Brookfield viscosity of 8000 cps at 25° C. (measured at 25% by weight neat polymer concentration);

KRATON G-1652 rubber, a SEBS copolymer having a styrene-ethylene/butylene ratio of 29/71, having a Shore A hardness of 75 and a Brookfield viscosity of 1350 cps at 25° C. (measured at 25% by weight neat polymer concentration).

C-FLEX™ R70-001(Concept Polymer Technologies), a material comprising a styrene-ethylene/butylene-styrene (SEBS) block copolymer modified with polypropylene, dimethylsiloxane, and mineral oil, and having a density of 0.90 g/cm$^3$ and a melt index of 0.25 g/10 min.

C-FLEX™ R70-051, a material comprising a SEBS block copolymer modified with polypropylene, mineral oil, and polymethyloctylsilane as described in U.S. Pat. No. 4,613,640 (Deisler et al., the entire disclosure of which is incorporated herein by reference), having a density of 0.90 g/cm$^3$ and melt index of 2.7 g/10 min.

C-FLEX™ R70-041, a material comprising a SEBS block copolymer modified with polypropylene and polydimethylsiloxane having a density of 0.90 g/cm$^3$.

C-FLEX™ R70-085, a material comprising a SEBS block copolymer modified with polypropylene, mineral oil, and siloxanes including polymethyloctylsiloxane and having a density of 0.90 g/cm$^3$.

C-FLEX™ R70-003, a material comprising a SEBS block copolymer modified with polydimethylsiloxane, polypropylene, and mineral oil, having a density of 0.90 g/cm$^3$.

C-FLEX™ R70-026, a material comprising a SEBS block copolymer modified with polypropylene, polydimethylsiloxane, and mineral oil, having a density of 0.90 g/cm$^3$.

When a diaphragm is incorporated into a valve and the valve is crimped onto an aerosol canister the diaphragm is compressed. The rubber comprising a SEBS copolymer is present in the blend in an amount effective to afford an elastomer having a hardness and elasticity such that a diaphragm will maintain at least about 80 percent of its original thickness when the valve is crimped into place. The amount that constitutes an effective amount can be readily selected by those skilled in the art and varies depending upon the particular polyolefin and the particular rubber in the blend. Generally, however, the blend comprises at least 10 parts by weight of the SEBS copolymer, more preferably at least 20 parts by weight, and most preferably at least 40 parts by weight.

The polyolefin component of the blend provides a semi-crystalline plastic matrix in which the rubber is substantially uniformly dispersed. In a substantially uniform dispersion the rubber particles preferably have an average size of less than about 10 μm, more preferably less than about 5 μm. It is preferred that the rubber be substantially nonagglomerated within the polyolefin matrix.

It has been found that excessive expansion or contraction of the diaphragm in an aerosol valve can result in an ineffective dynamic seal between the valve stem and the diaphragm. The blends defined above, however, have been found to be dimensionally stable when exposed to 1,1,1,2,-tetrafluoroethane or 1,1,1,2,3,3,3,-heptafluoropropane. It is preferred that the blend be stable to dimensional change (as that term is defined above) such that diaphragm dimensions change no more than about 8%, preferably no more than about 5 %, and most preferably no more than about 3%.

Shore A hardness of a blend for use in the invention is preferably between about 65 and about 85, more preferably between about 75 and 83. Also, it is preferred that the blend have a suitable compression set in order that the static seal between the diaphragm and the other components of the device (e.g., the valve ferrule and the metering tank of the device illustrated in the accompanying Drawing) remains adequate over the life of the device. Compression set can be measured by ASTM D 395 (incorporated by reference). Values of less than about 40, more preferably less than about 35, and most preferably less than about 20 are desirable (measured at 70 hours, 20° C. according to Method B of ASTM D 395).

Polymer blends from which sealing members can be made can be prepared by conventional polymer blending techniques well known to those skilled in the art, such as screw extrusion (single screw or twin screw), or in a blender. It is important, however, that the process used to blend the components affords a substantially uniform dispersion of the rubber in the polyolefin. Generally the blending is carried out at a temperature (e.g., 150° C. to 250° C.) high enough to soften the polymer components for blending but not so high as to degrade the polymer components. Blending is carried out for a time sufficient to afford a substantially uniform dispersion. Specific conditions will vary according to the particular components of the blend and can be readily selected by those skilled in the art.

Diaphragms can be prepared by conventional techniques known to those skilled in the art, such as compression molding, extrusion, and injection molding.

The device of the invention will be described with reference to the Drawing. FIG. 1 shows device 10 comprising valve stem 12, casing member 14, and diaphragm 16. The casing member has walls defining casing aperture 18, and the diaphragm has walls defining diaphragm aperture 17. The valve stem passes through and is in slidable sealing engagement with the diaphragm aperture. The diaphragm is also in sealing engagement with casing member 14. Diaphragm 16 represents an elastomeric sealing member. Such a sealing member can be one piece or it can be in the form of a plurality of thinner layers arranged in a stack.

The illustrated embodiment is a device for use with pharmaceutical formulations. The diaphragm in the illustrated embodiment is a single piece of a thickness sufficient to form an effective seal with the casing member, preferably about 0,125 mm (0.005 inch) to about 1.25 mm (0.050 inch). It has an outside diameter of about 8.6 mm (0.340 inch), and an inside diameter sufficient to form an effective seal with the valve stem. As valve stems having an outside diameter of about 2.79 mm (0.110 inch) are commonly used, suitable diaphragm inside diameter can be in the range of about 2.03 mm (0.080 inch) to about 2.67 mm (0.105 inch). Diaphragm dimensions suitable for use with other general types of devices can be easily selected by those skilled in the art.

Valve stem 12 is in slidable engagement with diaphragm aperture 17. Helical spring 20 holds the valve stem in an extended closed position as illustrated in FIG. 1. Valve stem 12 has walls defining orifice 22 which communicates with exit chamber 24 in the valve stem. The valve stem also has walls defining channel 26.

In the illustrated embodiment casing member 14 comprises mounting cup 28 and canister body 30 and defines formulation chamber 32. The illustrated embodiment further comprises tank seal 34 having walls defining tank seal aperture 35, and metering tank 36 having inlet end 38, inlet aperture 40, and outlet end 42. The metering tank also has walls defining metering chamber 44 of predetermined volume (e.g., 50 μL). Outlet end 42 of metering tank 36 is in sealing engagement with diaphragm 16, and valve stem 12 passes through inlet aperture 46 and is in slidable engagement with tank seal 34.

When device 10 is intended for use with a suspension aerosol formulation it further comprises retaining cup 46 fixed to mounting cup 28 and having walls defining retention chamber 48 and aperture 50. When intended for use with a solution aerosol formulation retaining cup 46 is optional. Also illustrated in device 10 is sealing member 52 in the form of an O-ring that substantially seals formulation chamber 32 defined by mounting cup 28 and canister body 30. Sealing member 52 preferably comprises the elastomer described above.

Operation of device 10 is illustrated in FIGS. 1 and 2. In FIG. 1, the device is in the extended closed position. Aperture 50 allows open communication between retention chamber 48 and formulation chamber 32, thus allowing the aerosol formulation to enter the retention chamber. Channel 26 allows open communication between the retention chamber and metering chamber 44 thus allowing a predetermined amount of aerosol formulation to enter the metering chamber through inlet aperture 40. Diaphragm 16 seals outlet end 42 of the metering tank.

FIG. 2 shows device 10 in the compressed open position. As valve stem 12 is depressed channel 26 is moved relative to tank seal 34 such that inlet aperture 40 and tank seal aperture 35 are substantially sealed, thus isolating a metered dose of formulation within metering chamber 44. Further depression of the valve stem causes orifice 22 to pass through aperture 18 and into the metering chamber, whereupon the metered dose is exposed to ambient pressure. Rapid vaporization of the propellant causes the metered dose to be forced through the orifice, and into and through exit chamber 24. Device 10 is commonly used in combination with an actuator that facilitates inhalation of the resulting aerosol by a patient.

A particularly preferred device of the invention is a metered dose configuration substantially as described above and illustrated in the Drawing. Other particular configurations, metered dose or otherwise, are well known to those skilled in the art and suitable. For example the devices described in U.S. Pat. Nos. 4,819,834 (Thiel), 4,407,481 (Bolton), 3,052,382 (Gawthrop), 3,049,269 (Gawthrop), 2,980,301 (DeGorter), 2,968,427 (Meshberg), 2,892,576 (Ward), 2,886,217 (Thiel), and 2,721,010 (Meshberg) (all incorporated herein by reference) involve a valve stem, a diaphragm, and a casing member in the general relationship described herein. Generally any and all sealing members (such as diaphragms, seals, and gaskets) that serve to minimize and/or prevent escape of components, especially propellant, from such assemblies can comprise the above described elastomer.

The devices of the invention find particular use with aerosol formulations involving a propellant comprising HFC-134a or HFC-227. Any such formulation can be used. Pharmaceutical formulations are preferred.

Preferred pharmaceutical formulations generally comprise HFC-134a or HFC-227 in an amount effective to function as an aerosol propellant, a drug having local or systemic action and suitable for use by inhalation, and any optional formulation excipients. Exemplary drugs having local effect in the lung include bronchodilators such as albuterol, formoterol, pirbuterol, and salmeterol, and pharmaceutically acceptable salts and derivatives thereof, and steroids such as beclomethasone, fluticasone, and flunisolide, and pharmaceutically acceptable salts, derivatives, solvates, and clathrates thereof. Exemplary drugs having systemic effect include peptides such as insulin, calcitonin, interferons, colony stimulating factors, and growth factors. The drug is present in the formulation in an amount sufficient to provide a predetermined number of therapeutically effective doses by inhalation, which can be easily determined by those skilled in the art considering the particular drug in the formulation. Optional excipients include those disclosed, e.g., in EP-A-372,777 (Purewal et al., incorporated herein by reference), and others known to those skilled in the art.

Depending upon the particular configuration of a device of the invention, a pharmaceutical aerosol formulation can be filled into an aerosol canister of the invention, e.g., by conventional pressure filling or cold filling methods. The formulation can then be administered by inhalation by coupling the aerosol canister to an aerosol actuator and dispensing the formulation via the actuator.

Test Methods

Diaphragms were tested as follows:
Leak Rate

Aerosol canister bodies (10 mL) are filled with an aerosol formulation and fitted with a metered dose valve substantially as described and illustrated above and comprising a diaphragm of a selected size and material. The valve is actuated several times in order to assure its function. The mass of the filled device is measured. The filled device is allowed to stand under the indicated conditions for a period of time, after which time mass is again measured. The loss of mass over time is extrapolated to one year and reported in mg/year.

As used in the claims below the "Leak Rate Test Method" involves twenty-five independent determinations as described above, using HFC-134a as the aerosol formulation and using a valve having a stainless steel valve stem with a 2.79 mm (0.110 inch) outside diameter and fitted with a diaphragm of the specified diaphragm material. The diaphragm is 0.89 mm (0.035 inch) thick having an inside diameter of 2.41 mm (0.095 inch), and having an outside diameter of 8.64 mm (0.34 inch).

Swelling

Diaphragms having a thickness of about 1.0 mm (0.040 inch), an inside diameter of about 2.5 mm (0.10 inch) and an outside diameter of about 8.6 mm (0.34 inch) are placed in a transparent closed measuring chamber (Comes Maschinenbou AG, Möhlin, Switzerland). The cell is filled with a soaking liquid and stored at the indicated temperature for the indicated period of time. The dimensions of the diaphragms are measured by viewing the diaphragms with a microscope through the window of the cell. Change of inside diameter and outside diameter is recorded as the average of three independent determinations.

Sidestreaming

An aerosol canister is held in an inverted position (valve down) in a beaker containing water. The water level is such that the casing aperture is submerged but the terminal edge of the mounting cup is not. The valve is actuated by depressing the valve stem against the bottom of the beaker. The source of bubbles is observed visually with the unaided eye. Sidestreaming is indicated if bubbles are observed emanating from the casing aperture. The absence of sidestreaming is indicated if bubbles emanate only from the valve stem.

EXAMPLES

Except as otherwise indicated blends containing a polyolefin component and a SEBS block copolymer component or a styrene-butadiene-styrene block copolymer component were prepared as a dry blend of the component polymers and blended by twin screw extrusion in a Berstdorff corotating intermeshing twin screw extruder (diameter: 40 mm; length to diameter ratio: 35; feed rate 6.8 kg/h; screw speed: 160 rpm; barrel temperature: 185° C.; feeder temperature: 50° C.). The resulting melt was extruded through a flat film die (282° C.) fitted with a shim to provide the desired opening and over a cooled roller. The thickness of the resulting sheet was controlled by appropriate selection of screw speed and roller speed. Other blends were prepared by twin screw extrusion using parameters selected according to the properties of the components of the blends.

Diaphragms were die cut and incorporated into a metered dose aerosol valve substantially as illustrated in the Drawing and comprising a stainless steel valve stem. The valves were crimped onto aerosol canisters and the canisters were filled with a placebo formulation containing 90% by weight 1,1,1,2-tetrafluoroethane and 10% by weight ethanol.

Certain properties of the blends were measured, and the aerosol canisters were tested for leak rate. Sidestreaming was also assessed. Results are shown in TABLES 1 and 2, wherein the absence of an entry indicates that no measurement was made.

TABLE 1

| Material | Diaphragm Number | Blend Ratio (by weight) | Compression Set (%) | Shore A Hardness | Leak Rate (mg/yr) | Sidestreaming Initial | 200 Shots |
|---|---|---|---|---|---|---|---|
| Buna[1] | 1 | — | 7.8 | 82 | 390 | none | — |
| FLEXOMER DFDB 1085 | 2 | — | 53 | 79 | 130 | all | — |
| FLEXOMER DFDB 1085/FLEXOMER DFDA 1137[5] | 3 | 100/11.1 | 35 | 82 | — | 12/20 | — |
|  | 4 | 100/25 | 36 | 85 | — | 15/20 | — |
|  | 5 | 100/43 | 38 | 87 | — | 10/20 | — |
|  | 6 | 100/67 | 39 | 89 | — | 7/20 | — |
|  | 7 | 100/100 | 38 | 91 | — | 7/20 | — |
| FLEXOMER DFDB 1085/KRATON D-1101[2] | 8 | 100/5.3 | 30 | 79 | $\ll 100^4$ | 11/20 | 10/20 |
|  | 9 | 100/11.1 | 30 | 78 | $\ll 100^4$ | 19/20 | 11/20 |
|  | 10 | 100/17.6 | 32 | 75 | $\ll 100^4$ | 17/20 | 15/20 |
|  | 11 | 100/25 | 33 | 76 | $\ll 100^4$ | 16/20 | 11/20 |
| FLEXOMER DFDB 1085/KRATON D-1102[3] | 12 | 100/5.3 | 32 | 79 | $\ll 100^4$ | 19/20 | 17/20 |
|  | 13 | 100/11.1 | 32 | 78 | $\ll 100^4$ | 11/20 | 9/20 |
|  | 14 | 100/17.6 | 34 | 76 | $\ll 100^4$ | 15/20 | 16/20 |
|  | 15 | 100/25 | 36 | 75 | $\ll 100^4$ | 14/20 | 19/20 |

[1]DB-218, commercially available from American Gasket and Rubber, Schiller Park, Illinois.
[2]A styrene-butadiene-styrene block copolymer, Shell Chemical.
[3]A styrene-butadiene-styrene block copolymer, Shell Chemical.
[4]Measured using an aerosol canister as illustrated in the drawing and comprising an additional o-ring seal crimped between the valve ferrule and the aerosol canister.
[5]Material made in single screw extruder.

TABLE 2

| Material | Diaphragm Number | Blend Ratio (by weight) | Compression Set (%) | Shore A Hardness | Leak Rate (mg/yr) | Sidestreaming Initial | 200 Shots |
|---|---|---|---|---|---|---|---|
| FLEXOMER DFDB 1085/KRATON G-1657 | 16 | 100/5.3 | 39 | 78 | <150 | — | — |
|  | 17 | 100/11.1 | 34 | 78 | <150 | — | — |
|  | 18 | 100/25 | — |  | <150 | — | — |
|  | 19 | 100/43 | — |  | <150 | — | — |
|  | 20 | 100/67 | — |  | <150 | — | — |
| FLEXOMER DFDB 1085/KRATON G-1650 | 21 | 100/5.3 | 30 | 78 | $\ll 100^1$ | — | 5/20 |
|  | 22 | 100/11.1 | 31 | 80 | $\ll 100^1$ | 0/20 | 0/20 |
|  | 23 | 100/17.6 | 29 | 77 | $\ll 100^1$ | 1/20 | 1/20 |
|  | 24 | 100/25 | 27 | 78 | $\ll 100^1$ | 0/20 | 0/20 |
| FLEXOMER DFDB 1085/KRATON G-1651 | 25 | 100/5.3 | 35 | 80 | $\ll 100^1$ | 11/20 | 12/20 |
|  | 26 | 100/11.1 | 30 | 80 | $\ll 100^1$ | 1/20 | 7/20 |
|  | 27 | 100/17.6 | 28 | 78 | $\ll 100^1$ | 1/20 | 3/20 |
| FLEXOMER DFDB 1085/KRATON G-1651 | 28 | 100/25 | 25 | 78 | $\ll 100^1$ | 0/20 | 0/20 |
|  | 29 | 100/25 | 26 | 77 | $\ll 100^1$ | 5/20 | — |
|  | 30 | 100/53.8 | 31 | 74 | $\ll 100^1$ | 0/20 | — |
| FLEXOMER DFDB 1085/FLEXOMER DFDA 1137/KRATON G-1651[2] | 31 | 44.4/55.5/11.0 | 39 | 89 | $\ll 100^1$ | 8/20 | — |
|  | 32 | 53.3/46.7/33 | 32 | 83 | $\ll 100^1$ | 0/20 | — |
|  | 33 | 67/33/67 | 26 | 77 | $\ll 100^1$ | 0/20 | — |
|  | 34 | 83.3/16.7/67 | 25 | 75 | $\ll 100^1$ | 0/20 | — |
|  | 35 | 70/30/33 | 25 | 81 | $\ll 100^1$ | 7/20 | — |
|  | 36 | 88.9/11.1/11.1 | 31 | 81 | $\ll 100^1$ | 14/20 | — |

[1]Measured using an aerosol canister as illustrated in the drawing and comprising an additional o-ring seal crimped between the valve ferrule and the aerosol canister.
[2]Single screw extruded.

The results in the TABLES indicate that aerosol canisters equipped with a diaphragm having more than 10 parts of SEBS block copolymer based on 100 parts by weight of polyolefin have lower leak rate than canisters equipped with Buna rubber diaphragms when used with the indicated formulation. Such blends exhibit less initial sidestreaming than the indicated polyolefins, polyolefin blends, and the blends involving a styrene-butadiene-styrene block copolymer. The results also show that those materials prepared in a single screw extruder do not function as well as those prepared using a twin screw extruder, due to the less effective dispersion of the rubber component by the single screw extruder.

The polyolefin/SEBS blend diaphragms 16–20 and 25–30 prepared above were tested generally according to the Swelling Test Method set forth above over a period or 11 days in HFC-134a and in a 90/10(w/w/) mixture of HFC-134a and ethanol. The diaphragms maintained their dimensions within one percent.

Polyolefin/SEBS blend diaphragms 25–30 prepared above were incorporated into a metered dose aerosol valve substantially as illustrated in the Drawing and comprising a stainless steel valve stem. The valves were crimped onto aerosol canisters and the canisters were filled with a formulation containing (by weight) HFC-134a (84.585%), ethanol (15.0%), oleic acid (0.03%), and albuterol sulfate (0.385%). Leak rate was less than 100 mg/yr.

The invention claimed is:

1. A device for delivering an aerosol, comprising: a valve stem, a diaphragm having walls defining a diaphragm aperture, and a casing member having walls defining a casing aperture, wherein the valve stem passes through the diaphragm aperture and the casing aperture and is in slidable sealing engagement with the diaphragm aperture, and wherein the diaphragm is in sealing engagement with the casing member and comprises a blend comprising (a) 100 parts by weight of a polyolefin random copolymer comprising about 80 to about 95 mole percent ethylene and a total of about 5 to about 20 mole percent of 1-butene, and (b) at least 10 parts by weight of a thermoplastic elastomer comprising a styrene-ethylene/butylene-styrene block copolymer based on 100 parts by weight of polyolefin, and wherein the styrene-ethylene/butylene-styrene block copolymer is uniformly dispersed within the polyolefin.

2. A device according to claim 1, further comprising: a tank seal having walls defining a tank seal aperture, and a metering tank having an inlet end, an inlet aperture, and an outlet end, wherein the outlet end is in sealing engagement with the diaphragm, the valve stem passes through the inlet aperture and the tank seal aperture and is in slidable engagement with the tank seal aperture, and the tank seal is in sealing engagement with the inlet end of the metering tank, and wherein the valve stem is movable between an extended closed position, in which the inlet end of the metering tank is open and the outlet end is closed, and a compressed open position in which the inlet end of the metering tank is sealed and the outlet end is open.

3. A device according to claim 2, wherein the casing member defines a formulation chamber.

4. A device according to claim 3, wherein the formulation chamber contains an aerosol formulation comprising 1,1,1,2,-tetrafluoroethane or 1,1,1,2,3,3,3-heptafluoropropane.

5. A device according to claim 4, wherein the formulation is a pharmaceutical formulation comprising 1,1,1,2,-tetrafluoroethane or 1,1,1,2,3,3,3-heptafluoropropane in an amount effective to function as an aerosol propellant, and a drug 6. A device according to claim 5, wherein the drug is albuterol sulfate.

7. A device according to claim 5, wherein the drug is beclomethasone dipropionate.

8. A device according to claim 5, wherein the drug is pirbuterol acetate.

9. A device according to claim 4, wherein the formulation further comprises a polar cosolvent.

10. A device according to claim 9, wherein the polar cosolvent is ethanol.

11. A device for delivering an aerosol, comprising:

a valve stem, a diaphragm that comprises (a) 100 parts by weight of a polyolefin random copolymer comprising about 80 to about 95 mole percent ethylene and a total of about 5 to about 20 mole percent of 1-butene, and (b) at least 10 parts by weight of a rubber comprising a styrene-ethylene/butylene-styrene block copolymer based on 100 parts by weight of polyolefin, and wherein the styrene-ethylene/butylene-styrene block copolymer is uniformly dispersed within the polyolefin, the diaphragm having walls defining a diaphragm aperture, and a casing member having walls defining a formulation chamber and a casing aperture, wherein the valve stem passes through the diaphragm aperture and the casing aperture and is in slidable sealing engagement with the diaphragm aperture, and wherein the diaphragm is in sealing engagement with the casing member, the device having contained in the formulation chamber thereof a medicinal aerosol formulation, and wherein the diaphragm is stable to dimensional change when exposed to the medicinal aerosol formulation.

12. A device according to claim 11, wherein the medicinal aerosol formulation comprises 1,1,1,2,-tetrafluoroethane or 1,1,1,2,3,3,3-heptafluoropropane.

13. A device according to claim 1, wherein the elastomer has a Shore A hardness of 65 to 85.

14. A device according to claim 1, wherein the elastomer has a Shore A hardness of 75 to 83.

15. A device according to claim 1, wherein the elastomer has a compression set of less than about 40.

\* \* \* \* \*